United States Patent
Rüfer et al.

(10) Patent No.: US 9,862,673 B2
(45) Date of Patent: Jan. 9, 2018

(54) 2-(3,3,5-TRIMETHYLCYCLOHEXYL) PROPANE-1,3-DIAMINE, A PROCESS FOR ITS PRODUCTION AND USE

(71) Applicant: Evonik Degussa GmbH, Essen (DE)

(72) Inventors: Alexander Martin Rüfer, Recklinghausen (DE); Anne Rittsteiger, Olfen (DE); Jörg-Joachim Nitz, Essen (DE); Stephan Kohlstruk, Gladbeck (DE); Martina Ortelt, Flein (DE); Dirk Fuchsmann, Haltern am See (DE); Michael Demming, Dülmen (DE); Christine Stemmer, Marl (DE); Denise Ott, Marl (DE); Anja Stasch, Recklinghausen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/604,873

(22) Filed: May 25, 2017

(65) Prior Publication Data

US 2017/0355661 A1    Dec. 14, 2017

(30) Foreign Application Priority Data

Jun. 10, 2016  (EP) .................................. 16173854

(51) Int. Cl.

| | | |
|---|---|---|
| *C07C 209/00* | (2006.01) | |
| *C07C 209/48* | (2006.01) | |
| *C07C 211/18* | (2006.01) | |
| *C07C 253/30* | (2006.01) | |
| *C08G 59/50* | (2006.01) | |
| *B01J 23/44* | (2006.01) | |
| *B01J 25/00* | (2006.01) | |

(52) U.S. Cl.
CPC ............ *C07C 209/48* (2013.01); *B01J 23/44* (2013.01); *B01J 25/00* (2013.01); *C07C 211/18* (2013.01); *C07C 253/30* (2013.01); *C08G 59/5026* (2013.01); *C07C 2601/14* (2017.05)

(58) Field of Classification Search
CPC .................................................. C07C 209/48
See application file for complete search history.

(56) References Cited

U.S. PATENT DOCUMENTS 5,373,068 A    12/1994  Piana et al.

FOREIGN PATENT DOCUMENTS

| EP | 0564818 A2 | 10/1993 |
|---|---|---|
| WO | 2016023837 A1 | 2/2016 |

OTHER PUBLICATIONS

Rios-Lombardia, et al. J. Org. Chem. 2009, 74, 2571-2574 2571.*
Langkabel et al., U.S. Appl. No. 15/602,723, filed May 23, 2017.
Langkabel et al., U.S. Appl. No. 15/603,966, filed May 24, 2017.
Langkabel et al., U.S. Appl. No. 15/604,118, filed May 24, 2017.
Rittsteiger et al., U.S. Appl. No. 15/473,892, filed Mar. 30, 2017.
Rüfer et al., U.S. Appl. No. 15/604,988, filed May 25, 2017.
Rüfer et al., U.S. Appl. No. 15/605,268, filed May 25, 2017.
European Search Report dated Nov. 15, 2016 in EP 16 17 3854 (1 page).

* cited by examiner

*Primary Examiner* — Sudhakar Katakam
*Assistant Examiner* — Ana Z Muresan
(74) *Attorney, Agent, or Firm* — Philip P. McCann; Smith Moore Leatherwood LLP

(57) ABSTRACT

A diamine 2-(3,3,5-trimethylcyclohexyl)propane-1,3-diamine of formula 1

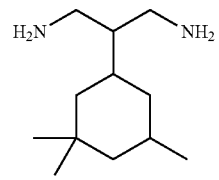

and a process for producing 2-(3,3,5-trimethylcyclohexyl) propane-1,3-diamine by A) reacting isophorone (IP) and malononitrile to afford the intermediate 2-(3,5,5-trimethylcyclohex-2-en-1-ylidene)malononitrile, and B) hydrogenating 2-(3,5,5-trimethylcyclohex-2-en-1-ylidene)malononitrile in the presence of at least one catalyst. In another embodiment, the hydrogenation in step B) of the process is performed at 20-120° C. and at 20-300 bar.

19 Claims, No Drawings

2-(3,3,5-TRIMETHYLCYCLOHEXYL) PROPANE-1,3-DIAMINE, A PROCESS FOR ITS PRODUCTION AND USE

This application claims the benefit of European Application No. 16173854.7 filed on Jun. 10, 2016, the disclosure of which is expressly incorporated herein by reference.

BACKGROUND

The present invention relates to a novel diamine having the name 2-(3,3,5-trimethylcyclohexyl)propane-1,3-diamine, referred to hereinbelow as CPDA, to a process for its production and to its use.

2-(3,3,5-trimethylcyclohexyl)propane-1,3-diamine (CPDA) has the chemical structure depicted in formula 1.

formula 1

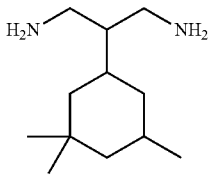

2-(3,3,5-trimethylcyclohexyl)propane-1,3-diamine (CPDA)

It is known that diamines may be employed as hardeners in epoxy systems. Epoxy resins are prepolymers comprising two or more epoxy groups per molecule. The reaction of these resins with a range of hardeners affords crosslinked polymers. An overview of possible resins and hardeners, their use and properties is given in H. Schumann, "*Handbuch Betonschutz durch Beschichtung*", Expert Verlag 1992, pages 396-428.

SUMMARY

It is an object of the invention to find a novel diamine suitable for hardening epoxy systems.

It is an object of the invention to find a process for producing 2-(3,3,5-trimethylcyclohexyl)propane-1,3-diamine (CPDA).

The invention provides the diamine 2-(3,3,5-trimethylcyclohexyl)propane-1,3-diamine (CPDA) conforming to formula 1.

DETAILED DESCRIPTION

The invention provides a process for producing 2-(3,3,5-trimethylcyclohexyl)propane-1,3-diamine by
  A) reacting isophorone (IP) and malononitrile to afford the intermediate 2-(3,5,5-trimethylcyclohex-2-en-1-ylidene)malononitrile, and
  B) hydrogenating 2-(3,5,5-trimethylcyclohex-2-en-1-ylidene)malononitrile in the presence of at least one catalyst.

The production of a compound according to the invention proceeds in the first step A) via a Knoevenagel condensation between isophorone (IP) and malononitrile. The reaction may be performed in a solvent or in a solvent-free reaction system under mild reaction conditions, preferably at 20-40° C. and atmospheric pressure. The catalyst employed is preferably zirconyl chloride or piperidine. After complete conversion of the reactants the intermediate 2-(3,5,5-trimethylcyclohex-2-en-1-ylidene)malononitrile (cf. structure in formula 2) may be precipitated out as solid by cooling the reaction solution. A further purification may be effected by distillation for example.

The production of CPDA from (3,5,5-trimethylcyclohex-2-en-1-ylidene)malononitrile is effected in step B) by hydrogenation which may be performed in one or more stages. When a plurality of hydrogenation reactions are used the individual stages may be performed in a reactor having different catalyst zones or in a plurality of separate or serially connected reactors.

The hydrogenation is preferably effected in fixed-bed reactors. Suitable reactor types are, for example, shaft furnaces, tray reactors or shell and tube reactors. It is also possible to connect a plurality of fixed-bed reactors in series for the hydrogenation, each of the reactors being operated in downflow mode or in upflow mode as desired.

The catalysts employed may in principle be any catalysts which catalyze the hydrogenation of nitrile groups with hydrogen. Particularly suitable catalysts are nickel, copper, iron, palladium, rhodium, ruthenium and cobalt catalysts, very particularly palladium, ruthenium and cobalt catalysts. To increase activity, selectivity and/or service life, the catalysts may comprise additional doping metals or other modifiers. Typical doping metals are, for example, Mo, Fe, Ag, Cr, Ni, V, Ga, In, Bi, Ti, Zr and Mn, and the rare earths. Typical modifiers are, for example, those with which the acid-base properties of the catalysts can be influenced, preferably alkali metals and alkaline earth metals or compounds thereof, preferably magnesium and calcium compounds, and also phosphoric acid or sulphuric acid and compounds thereof.

The catalysts may be employed in the form of powders or shaped bodies, for example extrudates or compressed powders. It is possible to employ unsupported catalysts, Raney-type catalysts or supported catalysts. Preference is given to Raney-type and supported catalysts. Suitable support materials are, for example, silicon dioxide, aluminium oxide, aluminosilicates, titanium dioxide, zirconium dioxide, kieselguhr, aluminium-silicon mixed oxides, magnesium oxide and activated carbon. The active metal can be applied to the support material in a manner known to those skilled in the art, for example by impregnation, spray application or precipitation. Depending on the method of catalyst production, further preparation steps known to those skilled in the art are necessary, for example drying, calcining, shaping and activation. Further assistants, for example graphite or magnesium stearate, may optionally be added for shaping. The required volume of the hydrogenation catalysts to be used is determined by the LHSV value (liquid hourly space velocity) which is dependent on operating pressure, temperature, concentration and catalyst activity and must be adhered to in order to ensure as complete a hydrogenation as possible.

Production of the inventive diamine CPDA preferably employs hydrogenation catalysts based on palladium and/or cobalt. These catalysts show particularly good activity to achieve a high yield. The catalysts may be employed in the form of powders or fixed-bed catalysts. The hydrogenation may be effected in batch mode or in continuously operated plants.

The reaction conditions for the hydrogenation are between 50-120° C. and 20-300 bar.

The hydrogenation may be performed in one or more stages. The hydrogenation is preferably performed in two stages. In the first of these stages, reaction conditions of 20-120° C. and 20-300 bar, preferably 40-100° C. and 25-150 bar and particularly preferably 60-90° C. and 40-80 bar are chosen. In the second stage of the hydrogenation, reaction conditions of 20-120° C. and 20-300 bar, preferably 50-115° C. and 50-200 bar and particularly preferably 80-110° C. and 80-140 bar are chosen.

The first stage of the hydrogenation preferably employs a palladium catalyst.

The second stage of the hydrogenation preferably employs a Raney-type catalyst. It is particularly preferable when after activation the catalyst in its entirety has the following composition in weight per cent (wt %), the proportions summing to 100 wt % based on the metals present:

cobalt: 57 to 84 wt %
aluminium: 10 to 40 wt %
chromium: 1 to 2 wt %
nickel: 2 to 4 wt % and with particle sizes of the catalyst, i.e. of the pellet particles, having a statistical distribution between 3 to 7 millimetres (mm), wherein up to 10 per cent of the particles may also be outside the stated range of the stated lower limit or upper limit but also in each case up to 10 per cent may be outside the stated range of the stated lower limit and upper limit.

The reaction mixture leaving the hydrogenation is further purified by customary methods to obtain CPDA of the desired quality. Any standard separation methods, for example distillation, flash evaporation, crystallization, extraction, sorption, permeation, phase separation or combinations of the above, may be employed here. The purification may be conducted continuously, batchwise, in one or more stages, under vacuum or under pressure.

The purification is preferably achieved by distillation under pressure and/or under vacuum in a plurality of steps. Any desired distillation columns with or without internals may be used to this end, for example dephlegmators, dividing walls, unordered internals or random packings, ordered internals or structured packings, or trays with or without forced flow. The purification of CPDA is preferably performed by distillation.

Use as Epoxy Hardener

The invention also provides for the use of 2-(3,3,5-trimethylcyclohexyl)propane-1,3-diamine (CPDA) as a hardener in epoxy resin compositions.

Contemplated as the epoxy resin component are in principle all epoxy resins that may be cured with amines. Epoxy resins include, for example, polyepoxides based on bisphenol A diglycidyl ether, bisphenol F diglycidyl ether or cycloaliphatic types. However, preference is given to using epoxy resins based on bisphenol A and optionally those based on bisphenol F, optionally also in admixture. The resins and hardeners are preferably employed in equivalent amounts. However, deviations from the stoichiometric ratio are also possible.

EXAMPLES

Example 1: Production of 2-(3,3,5-trimethylcyclohexyl)propane-1,3-diamine (CPDA)

Step A): Synthesis of 2-(3,5,5-trimethylcyclohex-2-en-1-ylidene)malononitrile.

Formula 2

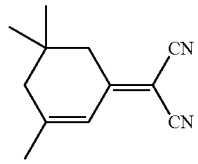

2-(3,5,5-trimethylcyclohex-2-en-1-ylidene)malononitrile

A 2 L three-necked flask fitted with two dropping funnels was initially charged with 484 g of isophorone (IP). The reactor contents were kept at room temperature.

231 g of malononitrile were diluted with 250 g of ethanol (EtOH) and initially charged into a dropping funnel.

7 g of piperidine (catalyst) were diluted with 50 g of EtOH and filled into the second dropping funnel.

The contents of both dropping funnels were then simultaneously added dropwise to the reactor and the reactor was then stirred for two hours at 50° C.

The reaction mixture formed was cooled to 10° C. and the thus precipitated product (2-(3,5,5-trimethylcyclohex-2-en-1-ylidene)malononitrile) was filtered off.

The further purification was effected by recrystallization in cold ethanol and subsequent filtration and drying in a vacuum drying cabinet (45° C., 10 mbar, 3 h).

The product composition was determined by gas chromatography.

The yield of 2-(3,5,5-trimethylcyclohex-2-en-1-ylidene)malononitrile was 50%.

Step B1): Partial Hydrogenation of 2-(3,5,5-trimethylcyclohex-2-en-1-ylidene)malononitrile to Produce CPDA, 1st Hydrogenation Stage.

150 ml of the fixed-bed catalyst Pd/aluminium oxide (1 wt % Pd) was installed in a 2 L pressure autoclave fitted with a catalyst cage.

1 L of solution comprising 10 wt % of 2-(3,5,5-trimethylcyclohex-2-en-1-ylidene)malononitrile (product from step A) in tetrahydrofuran was initially charged for the reaction.

The reaction was effected at 75° C. with 50 bar of hydrogen for 5 h.

The entire product solution was discharged from the reactor.

The composition of the product solution was determined by gas chromatography.

Step B2) 2nd Hydrogenation Stage: Full Hydrogenation of Product Solution From Step B.

150 ml of activated Raney cobalt alloy pellets were installed as a fixed bed in a 2 L pressure autoclave fitted with a catalyst cage. This catalyst had the following composition in weight per cent (wt %), the proportions summing to 100 wt % based on the metals present:
cobalt: 75.9 wt %
aluminium: 20.0 wt %
chromium: 1.5 wt %
nickel: 2.6 wt %

A sieve fraction of the catalyst having a statistical distribution between 2.0 and 5.0 millimetres (mm) was employed, wherein up to 10% of the particles may be above the stated upper limit and up to 10% of the particles may be below the stated lower limit.

1 L of reaction solution (partially hydrogenated product from step B1 in THF) was initially charged for the reaction.

The reaction was effected at 100° C. with 100 bar of hydrogen for 5 h.

The composition of the product solution was determined by gas chromatography.

For use of CPDA as a hardener in epoxy resin systems the product obtained was purified by distillation.

The yield of the two-stage hydrogenation (steps B1 and B2) was 83 wt % of CPDA based on the employed dinitrile from stage A.

Example 2: CPDA as a Hardener in Epoxy Resin Systems

The epoxy resin employed was the standard resin Epikote 828 from Hexion having an epoxy equivalent weight of 188 g/eq. Said resin was blended in stoichiometric equality of the H equivalents with the hardener component CPDA (cf. Table 1) and the glass transition temperature (Tg) was determined after a dwell time of one hour at a defined curing temperature (Table 2). The respective reaction conversions were determined via the recorded evolution of heat from the curing reaction in relation to the maximum evolution of heat (Table 3).

TABLE 1

Ratio of resin to hardener

| | |
|---|---|
| Hardener component CPDA (g) | 100 |
| Amount of epoxy resin (g) per 100 g of hardener | 380 |

TABLE 2

Glass transition temperatures (Tg) after one hour of curing at various temperatures

| | |
|---|---|
| Tgmax. (DSC) | 135° C. |
| Tg after 1 h 50° C. | 47° C. |
| Tg after 1 h 70° C. | 75° C. |
| Tg after 1 h 90° C. | 97° C. |
| Tg after 1 h 110° C. | 117° C. |
| Tg after 1 h 130° C. | 130° C. |
| Tg after 1 h 150° C. | 134° C. |

TABLE 3

Conversions

| | |
|---|---|
| Conversion after 1 h 50° C. | 90% |
| Conversion after 1 h 70° C. | 90% |
| Conversion after 1 h 90° C. | 92% |
| Conversion after 1 h 110° C. | 100% |
| Conversion after 1 h 130° C. | 100% |
| Conversion after 1 h 150° C. | 100% |

As is readily apparent to a person skilled in the art from Table 1, Table 2 and Table 3, CPDA is a suitable hardener component in epoxy resin systems.

The invention claimed is:

1. A diamine 2-(3,3,5-trimethylcyclohexyl)propane-1,3-diamine of formula 1

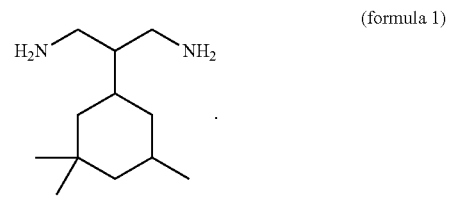
(formula 1)

2. A process for producing 2-(3,3,5-trimethylcyclohexyl)propane-1,3-diamine of formula 1

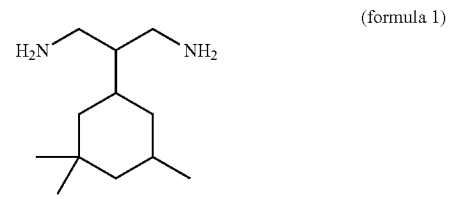
(formula 1)

the process comprising the steps of
A) reacting isophorone (IP) and malononitrile to produce an intermediate 2-(3,5,5-trimethylcyclohex-2-en-1-ylidene)malononitrile, and
B) hydrogenating the intermediate 2-(3,5,5-trimethylcyclohex-2-en-1-ylidene)malononitrile in the presence of at least one catalyst.

3. The process according to claim 2, wherein the hydrogenation in step B) is performed at from 20-120° C. and at from 20-300 bar.

4. The process according to claim 2, wherein the hydrogenation in step B) is performed in two stages at from at 40-100° C. and at from 25-150 bar.

5. The process according to claim 4, wherein the hydrogenation in step B) is performed in two stages at from 20-120° C. and at from 20-300 bar.

6. The process according to claim 4, wherein the hydrogenation is performed at from 40-100° C. and from 25-150 bar in the first stage and at from 50-115° C. and from 50-200 bar in the second stage.

7. The process according to claim 4, wherein the hydrogenation is performed at from 60-90° C. and from 40-80 bar in the first stage and at from 80-110° C. and from 80-140 bar in the second stage.

8. The process according to claim 2, wherein the at least one catalyst is selected from nickel, copper, iron, palladium, rhodium, ruthenium or cobalt catalysts.

9. The process according to claim 2, wherein the at least one catalyst are palladium and/or cobalt catalysts.

10. The process according to claim 2, wherein the at least one catalyst are Raney-type catalysts or supported catalysts.

11. The process according to claim 2, wherein the at least one catalyst is a catalyst composed of activated Raney cobalt alloy pellets, wherein after activation the catalyst in its entirety has the following composition in weight per cent (wt %), the proportions summing to 100 wt % based on the metals present:

cobalt: 57 to 84 wt %
aluminium: 10 to 40 wt %
chromium: 1 to 2 wt %
nickel: 2 to 4 wt % and
with particle sizes of the catalyst, or the pellet particles, having a statistical distribution between 3 to 7 millimetres (mm), wherein up to 10 per cent of the particles may also be outside the stated range of the stated lower limit or upper limit but also in each case up to 10 per cent may be outside the stated range of the stated lower limit and upper limit.

12. The process according to claim 2, wherein the hydrogenation is performed in fixed-bed reactors.

13. The process according to claim 3, wherein the at least one catalyst is selected from the group consisting of nickel, copper, iron, palladium, rhodium, ruthenium or cobalt catalysts.

14. The process according to claim 3, wherein the at least one catalyst is palladium and/or cobalt catalysts.

15. The process according to claim 3, wherein the at least one catalyst are Raney-type catalysts or supported catalysts.

16. The process according to claim 3, wherein the at least one catalyst is a catalyst composed of activated Raney cobalt alloy pellets, wherein after activation the catalyst in its entirety has the following composition in weight per cent (wt %), the proportions summing to 100 wt % based on the metals present:
cobalt: 57 to 84 wt %
aluminium: 10 to 40 wt %
chromium: 1 to 2 wt %
nickel: 2 to 4 wt % and
with particle sizes of the catalyst, or the pellet particles, having a statistical distribution between 3 to 7 millimetres (mm), wherein up to 10 per cent of the particles may also be outside the stated range of the stated lower limit or upper limit but also in each case up to 10 per cent may be outside the stated range of the stated lower limit and upper limit.

17. The process according to claim 2, wherein the hydrogenation in step B) is performed in fixed-bed reactors selected from the group consisting of shaft furnaces, tray reactors or shell and tube reactors.

18. The process according to claim 5, wherein at least one catalyst selected from the group consisting of nickel, copper, iron, palladium, rhodium, ruthenium or cobalt catalysts.

19. The process according to claim 5, wherein the at least one catalyst is palladium and/or cobalt catalysts.

* * * * *